United States Patent
Hine et al.

(10) Patent No.: US 6,889,091 B2
(45) Date of Patent: May 3, 2005

(54) METHOD AND APPARATUS FOR PLACING A CORONARY SINUS/CARDIAC VEIN PACING LEAD USING A MULTI-PURPOSE SIDE LUMEN

(75) Inventors: Douglas S. Hine, White Bear Lake, MN (US); Vicki L. Bjorklund, Maple Grove, MN (US); John L. Sommer, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 253 days.

(21) Appl. No.: 10/094,437

(22) Filed: Mar. 6, 2002

(65) Prior Publication Data

US 2003/0171796 A1 Sep. 11, 2003

(51) Int. Cl.$^7$ ................................................. A61N 1/05
(52) U.S. Cl. ........................................................ 607/119
(58) Field of Search ................................. 607/115–156

(56) References Cited

U.S. PATENT DOCUMENTS

| | | |
|---|---|---|
| 4,467,817 A | 8/1984 | Harris |
| 4,497,326 A | 2/1985 | Curry |
| 4,991,578 A | 2/1991 | Cohen |
| 5,033,998 A | 7/1991 | Corday et al. |
| 5,305,745 A | 4/1994 | Zacouto |
| 5,368,564 A | 11/1994 | Savage |
| 5,423,878 A | 6/1995 | Franz |
| 5,451,233 A | 9/1995 | Yock |
| 5,507,725 A | 4/1996 | Savage et al. |
| 5,531,679 A | 7/1996 | Schulman et al. |
| 5,571,085 A | 11/1996 | Accisano, III |
| 5,571,161 A | 11/1996 | Starksen |
| 5,681,278 A | 10/1997 | Igo et al. |
| 5,800,498 A | 9/1998 | Obino et al. |
| 6,659,981 B2 | 12/2003 | Stewart et al. ......... 604/164.02 |
| 2002/0019632 A1 | 2/2002 | Altman et al. |
| 2003/0032936 A1 * | 2/2003 | Lederman .................... 604/507 |
| 2003/0074041 A1 * | 4/2003 | Parry et al. ................. 607/130 |

FOREIGN PATENT DOCUMENTS

WO    WO 95/13111    5/1995

OTHER PUBLICATIONS

Physician's Manual, *EASYTRAK*™, Coronary Venous Steroid–Eluting Unipolar Pace/Sense Lead.
*Medtronic Technical Manual*, "Transvenous, unipolar, left ventricular, guidewire delivered, cardiac vein pacing lead", Feb. 23, 1999.
*Medtronic Technical Manual*, "Steroid eluting, transvenous, unipolar, left ventricular, cardiac vein pacing lead", Sep. 8, 1999.

* cited by examiner

*Primary Examiner*—Scott M. Getzow
(74) *Attorney, Agent, or Firm*—Girma Wolde-Michael

(57) ABSTRACT

A medical electrical lead, which may be useful in coupling an implantable medical device, is comprised of an elongate body having first and second spaced apart lumens. A conductor and an electrode are associated with the first lumen, and the second lumen is multi-purpose. The second lumen may be used to guide the lead and to introduce various fluids into the venous system. The second lumen may at various times be used to introduce vasodilation solutions, contrast fluids and adhesives into the venous system.

1 Claim, 3 Drawing Sheets

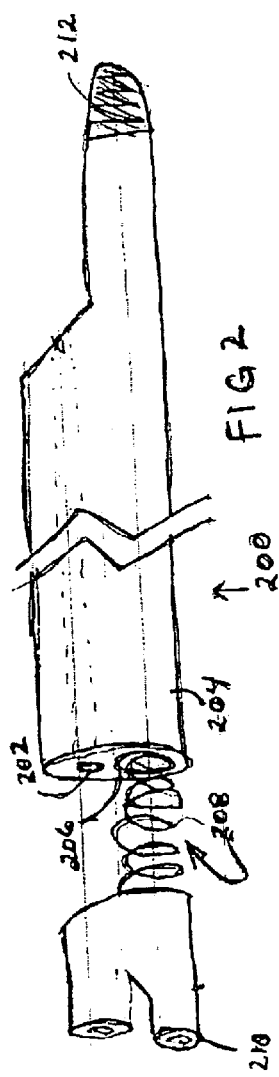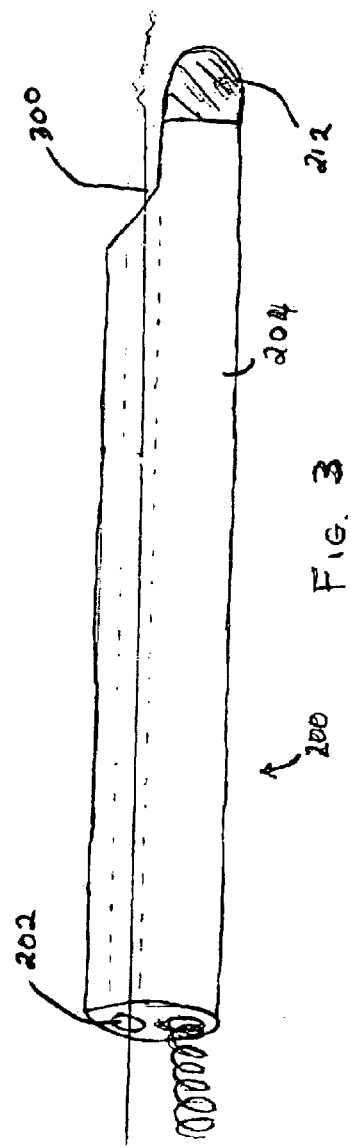

METHOD AND APPARATUS FOR PLACING A CORONARY SINUS/CARDIAC VEIN PACING LEAD USING A MULTI-PURPOSE SIDE LUMEN

FIELD OF THE INVENTION

This invention relates generally to implantable cardiac leads, and, more particularly, to a guided implantable cardiac lead with a multi-purpose side lumen.

DESCRIPTION OF THE RELATED ART

Since the introduction of the first implantable pacemakers in the 1960s, there have been considerable advancements in both the field of electronics and medicine, such that there is presently a wide assortment of commercially available implantable electronic medical devices. The class of implantable medical devices now includes therapeutic and diagnostic devices, such as pacemakers, cardioverters, defibrillators, neural stimulators, and drug administering devices, among others. Today's state-of-the-art implantable medical devices are vastly more sophisticated and complex than their early counterparts, and are capable of performing significantly more complex tasks. The therapeutic benefits of such devices have been well proven.

Modern electrical therapeutic and diagnostic devices for the heart require a reliable electrical connection between the device and a region of the heart. Typically, a medical electrical contact, commonly referred to as a "lead," is used for the desired electrical connection. One type of commonly used implantable lead is a transvenous lead. Transvenous leads are positioned through the venous system to attach and/or electrically connect at their distal end to the heart. At their proximal end, they are typically connected to the electrical therapeutic and/or diagnostic device, which may be implanted. Such leads normally take the form of a long, generally straight, flexible, insulated conductor. Among the many advantages of transvenous leads is that they permit an electrical contact with the heart without physically exposing the heart itself, i.e., major thoracic surgery is not required.

The specific design of transvenous leads is varied, depending upon the region of the heart to which it is to be connected. A variety of mechanisms and procedures have been proposed for easing the difficult and time-consuming task of guiding the leads through the cardiac venous system. Generally, owing to patient-to-patient variations in the anatomy of the cardiac venous system, it is difficult for the surgeon to visualize and/or identify the location of the lead as it is guided through the cardiac venous system. Accordingly, it should be appreciated that guiding the lead through the appropriate veins to arrive at a desired location is difficult, requiring much trial and error with many repetitive and unsuccessful manipulations of the leads. Improving a surgeon's ability to visualize and identify the location of the leads as well as the appropriate path through the cardiac venous system may dramatically ease the process of guiding the leads to their desired location.

SUMMARY OF THE INVENTION

In one aspect of the present invention, a method is provided for positioning a medical electrical lead in a venous system generally, and a cardiac venous system in particular. According to a preferred embodiment, the method includes inserting a lead within the cardiac venous system wherein the lead includes first and second spaced apart lumens extending between proximal and distal end portions of the lead. The lead is guided into the cardiac venous system using a guide element positioned in the second lumen. A fluid is introduced into the second lumen at the proximal end portion of the lead and dispensed from the second lumen adjacent the distal portion of the lead.

In another aspect of the present invention, a medical electrical lead is provided. The medical electrical lead is comprised of an elongate body, a first electrode, and a conductor. The elongate body has a proximal and a distal end portion and a first and second lumen extending longitudinally therebetween. The second lumen has an opening extending to an outer surface of the medical electrical lead. The first electrode is coupled adjacent the distal end portion of the elongate body, and a conductor extends between the proximal and distal end portions of the elongate body within the first lumen and is coupled to the electrode.

BRIEF DESCRIPTION OF THE DRAWINGS

The invention may be understood by reference to the following description taken in conjunction with the accompanying drawings, in which like reference numerals identify like elements, and in which:

FIG. 2 schematically illustrates a portion of an implantable lead with a multi-purpose side lumen;

FIG. 3 schematically illustrates the lead of FIG. 2 with a guidewire extending through the multi-purpose side lumen;

Figure 1:
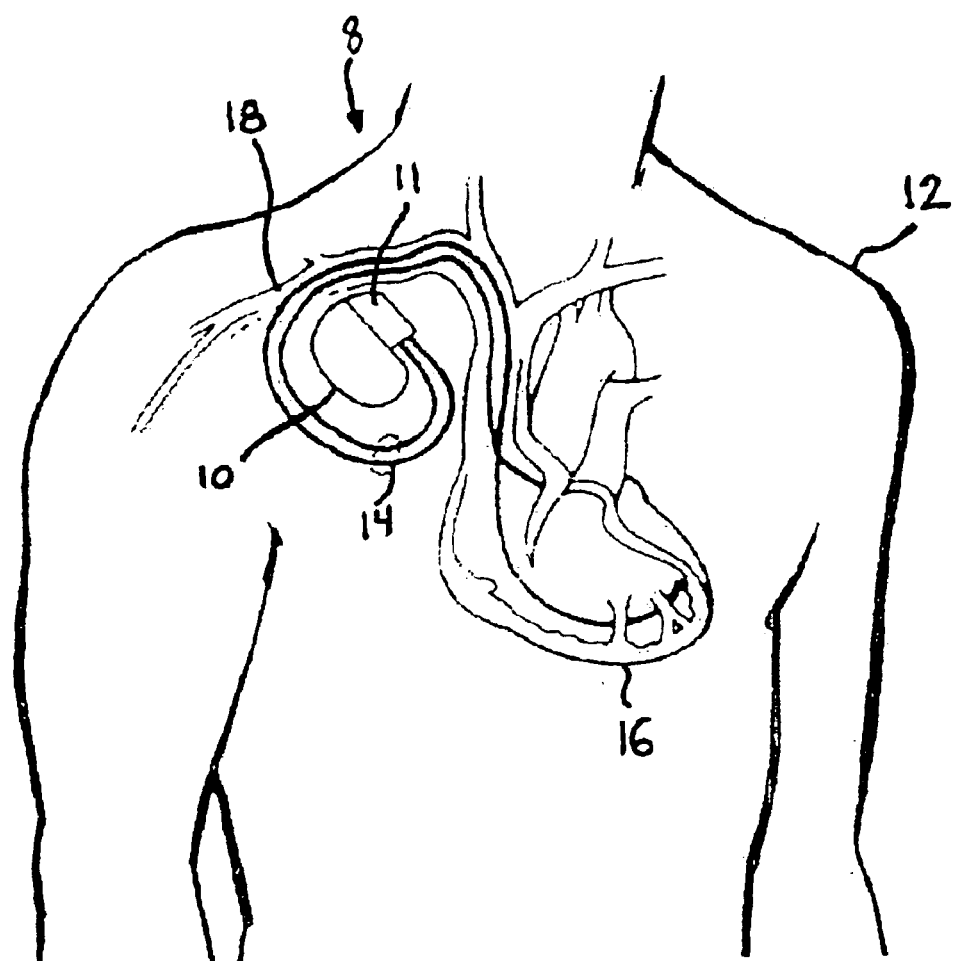
FIG. 1 schematically illustrates one embodiment of an implanted medical device in the form of a pacemaker and associated leads positioned to stimulate and/or sense the heart.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but, on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention concerns a lead that may preferably be implanted and used to stimulate and/or sense the atrium and ventricle of the left side of the heart through a cardiac venous system, such as the coronary sinus and its tributaries.

As is well known, there has to date been great difficulty in quickly and accurately guiding leads within the coronary sinus. Variations among patients in the anatomy of the coronary sinus and the heart may be accommodated by improving visualization of the position of the lead as well as the anatomy of the coronary sinus. Further, a temporary localized enlargement of the coronary veins may ease the process of guiding the lead therethrough Thus, the present invention includes a lead with a multi-purpose side lumen that may be used at different times to guide the lead, to introduce a contrast medium within the vein to improve visualization, to introduce a vasodilation solution to temporarily and locally dilate the veins to guide the lead through the coronary vein with a high degree of efficiency and accuracy, and to inject adhesive to fixate the lead within the coronary vein.

FIG. 1 illustrates an implantable medical device (IMD) system 8, which includes an implantable electronic device 10, such as a pacemaker, defibrillator, or the like, that has been implanted in a patient 12. The device 10 is housed within a hermetically sealed, biologically inert outer canister or housing, which may itself be conductive so as to serve as an electrode in the pacemaker's pacing/sensing circuit. One or more pacemaker leads, collectively identified with reference numeral 14 in FIG. 1 are electrically coupled to the pacemaker 10 in a conventional manner and extend into the patient's heart 16 via a vein 18. Disposed generally near a distal end of the leads 14 are one or more exposed conductive electrodes for sensing cardiac activity, delivering electrical pacing stimuli to the heart 16, and/or providing one or more stimulating voltage signal(s) to defibrillate the heart 16. The leads 14 may be implanted with their distal end situated on one or more of a plurality of locations, such as adjacent to the atrium or the ventricle, or both, of the heart 16.

In the embodiments illustrated herein, some variation in the location of the leads 14 may be useful in adapting the leads to their intended use. That is, the positioning of the leads 14 may be altered when the leads 14 are used to variously provide left ventricle and atrial pacing, coronary sinus defibrillation, and/or left ventricle defibrillation. The process used to position the leads at the various locations is relatively similar. The method and apparatus useful in performing the various aspects of the implanting and positioning of the leads 14 are described in greater detail below in conjunction with FIGS. 2–4.

To the extent that certain components and procedures referenced herein are conventional in their design and operation, such components/procedures will not be described herein in detail, as it is believed that design and implementation of such components and the performance of such methods would be a matter of routine practice to those of ordinary skill in the art. For example, various processes for passing a catheter lead through the tortuous path of a representative cardiac venous system is well known in the art.

FIG. 2 provides a stylized view of an implantable lead 200 with a multi-purpose side lumen 202. The lead 200 comprises an elongated, generally tubular body 204, which may be constructed from a silicone rubber, polyurethane, or other implantable material. As revealed by the partial cross sectional end view through the body 204, two passages or lumens are provided, a main lumen 206 and the side lumen 202. The main lumen 206 houses a coiled conductor 208 that extends the length of the body 204, from a connector 210 (e.g., and IS-1 type connector) at its proximal end to an electrode 212 physically coupled to its distal end. The electrode 212 may be formed from a conductive material, such as a platinum alloy or other biocompatible metal.

Generally, the electrode 212 may be used to sense electrical activity associated with a chamber of the heart adjacent thereto and/or to deliver electrical stimulation to the adjacent chamber of the heart. For example, the device 10 may produce pacing stimuli, which are delivered through the connector 210, the coiled conductor 208, and the electrode 212 to the heart 16. Alternatively, electrical activity resulting from muscular contractions in the heart 16 may be detected by the electrode 212 and passed through the coiled conductor 208 and the connector 210 to the device 10.

The side lumen 202 is formed within the body 204 generally parallel to the main lumen 206 and terminates adjacent the electrode 212 at the distal end of the lead 200, as shown, or may extend through the electrode 212. The side lumen 202 may have a variety of cross sectional configurations, such as round, oval, or other closed polyhedrons, and is a generally open port at the distal end of the lead 200. Thus, fluids, guidewires, and the like that may be introduced into the side lumen at the proximal end of the lead 200 may travel the length of the side lumen 202 and exit the lead 200 at its distal end. In the illustrated embodiment, the side lumen 202 terminates in a smooth tapered surface adjacent the distal end of the lead 200. The smooth taper advantageously eases movement of the lead 200 through the coronary sinus and its tributary veins.

A physician directing the lead 200 through the coronary sinus of a patient may advantageously employ the side lumen to perform a variety of tasks. For example, a conventional percutaneous transluminal catheter angioplasty (PTCA) guide wire, deflectable wire, or stylet may be passed through the side lumen 202 to allow the physician to guide the lead 200 through the various branches of the coronary sinus to position the lead 200 at a desired location. Additionally, the side lumen 202 may be used to introduce a vasodilation solution into the coronary sinus to temporarily dilate the local vein to ease passage of the lead 200 therethrough. Similarly, a contrast medium may also be delivered through the side lumen 202 to identify the location of the electrode 212 within the coronary sinus and/or to more clearly show the anatomy of the coronary veins. Further, once the lead 200 is properly positioned within the coronary sinus, the electrode 212 may be fixed in place by introducing a bonding substance or adhesive, such as cyanocrylate, through the side lumen 202. The adhesive may be used to adhere the lead 200 to the coronary sinus tissue, or to adhere the lead 200 to the cardiac vessel, in a region adjacent the open port of the side lumen 202.

Turning now to FIG. 3, a stylized view of the lead 200 with a guidewire 300 extending through the multi-purpose side lumen 202 is shown. The guidewire 300 may have been previously inserted into the coronary sinus and its tributaries using conventional techniques such that it passes therethrough to a region adjacent the heart. Thereafter, guidewire 300 may be backfed through the side lumen 202 as the lead 200 is urged further into the coronary sinus. The side lumen 202 tracks the guidewire 300, allowing the relatively large lead 200 to be readily guided along the same path earlier traversed by the relatively small guidewire 300.

Alternatively, a conventional stylet (not shown) may be used, alone or in conjunction with the guidewire 300 in the side lumen 202, to guide the lead 200 through the appropriate branches and sub-branches of the coronary sinus. The use of stylet to guide a lead 200 through the coronary sinus is well known to those of ordinary skill in the art, and thus will not be discussed in detail herein so as to avoid unnecessarily obscuring the instant invention. Generally, when the stylet is used alone, the physician slowly feeds the lead 200 into the coronary sinus until the distal end portion of the lead 200 reaches a branch or sub-branch into which it needs to be guided. The surgeon then shapes or otherwise bends at least an end portion of a stylet such that the bend in the stylet will cause the distal end of the lead 200 to turn or otherwise curve as the bent stylet passes into the distal end portion. The surgeon then feeds the bent stylet through the conductor lumen 208, causing the distal end portion of the lead 200 to turn in a direction toward the desired branch or sub-branch. Thereafter, as the physician feeds the lead 200 further into the coronary sinus it follows the now curved path leading into the desired branch or sub-branch. This process may be repeated each time that the vein curves or otherwise changes paths.

In applications where the stylet is used in combination with the guidewire 300, the process of guiding the lead 200 is similar. The combined use of the guidewire 300 and the stylet, however, offers advantages over either technique used alone. For example, the physician may use the stylet to push the lead 200 by bottoming the stylet against the distal end portion of the conductor lumen 208, and to steer the distal end portion of the lead 200 by shaping the stylet. Alternatively, the bent stylet may be withdrawn slightly from the distal end portion of the lead 200, resulting in the distal end portion of the lead 200 being more flexible. The physician may then advance the lead 200 along the guidewire 300 without pushing the stylet. This approach is particularly effective when guiding the lead 200 through an acute angle bend in the coronary sinus. Once the acute angle has been negotiated, the lead 200 may again be advanced by pushing with the stylet.

Figure 4:
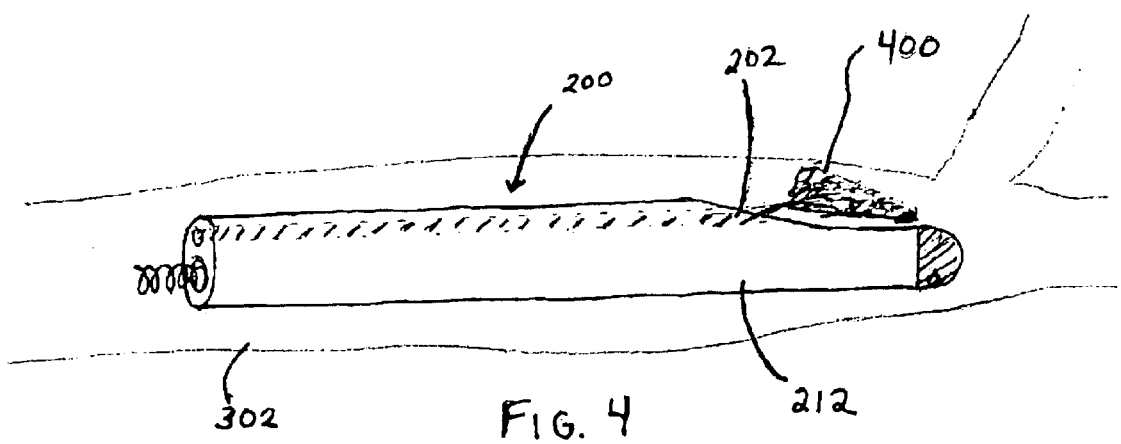
FIG. 4 schematically illustrates the lead of FIG. 2 with a contrast medium or vasodilation solution being introduced through the multi-purpose side lumen.

Turning now to FIG. 4, a stylized view of the lead 200 positioned adjacent a branch in the coronary sinus 302 is shown. According to the present invention, a fluid is introduced into the side lumen 202 at the proximal end portion of the lead 200 and dispensed from the side lumen 202 adjacent the distal portion of the lead 200. For example, according to a preferred embodiment of the present invention, the position of the lead 200 and the anatomy of the coronary sinus 302 may be determined by delivering a contrast fluid 400, such as fluoroscopic dye through the side lumen 202. The contrast fluid 400 will enter the blood stream within the coronary sinus 302 at a point adjacent the electrode 212 of the lead 200 and be carried by blood flowing therethrough throughout the various downstream branches in the coronary sinus 302. A fogram may be obtained by the physician to detect the presence of the contrast fluid 400 in the veins of the patient. In fact, a "picture" of the contrast fluid 400 within the coronary sinus 302 is produced. Thus, since the contrast fluid 400 has mixed with the blood and effectively filled the local veins, the "picture" of the contrast fluid substantially accurately represents the anatomy of the veins in the local region immediately downstream of the electrode 212. The physician may use this capability of the lead 200 to periodically visualize the position of the distal end portion of the lead 200 and to identify branches and sub-branches of the coronary sinus through which he/she intends to direct the lead 200. These "pictures" may be used to select the appropriate path for the lead 200 and/or to confirm that the lead 200 has been effectively guided into the appropriate branch or sub-branch of the coronary veins.

As the lead 200 is guided through the various veins of the coronary sinus 302, it may pass through several areas of restricted size. For example, as the lead 200 passes through regions of the venous system that turn relatively sharply or through regions of restricted diameter, the size of the vein may be sufficiently small to constrain the lead against free movement therethrough. Where there is insufficient spacing to allow the lead 200 to pass freely through a restricted region of the venous system, the physician may elect to backtrack and attempt an alternative path, or more force may be applied to the lead 200 to urge the lead through the restricted region. Alternatively, in the instant apparatus, a vasodilation solution, such as nitroglycerin solutions, angiotensin converting enzyme (ace) inhibitor solutions, and the like, may be delivered to the restricted area through the side lumen 202 by introducing the vasodilation solution at the proximal end portion of the lead 200 and dispensing the vasodilation solution from the side lumen 202 adjacent the distal end portion of the lead 200. The vasodilation solution may cause the vein, at least locally, to dilate, allowing freer movement of the lead 200 through the restricted region. In this manner, fewer traumas may be inflicted upon the venous system.

Figure 5:
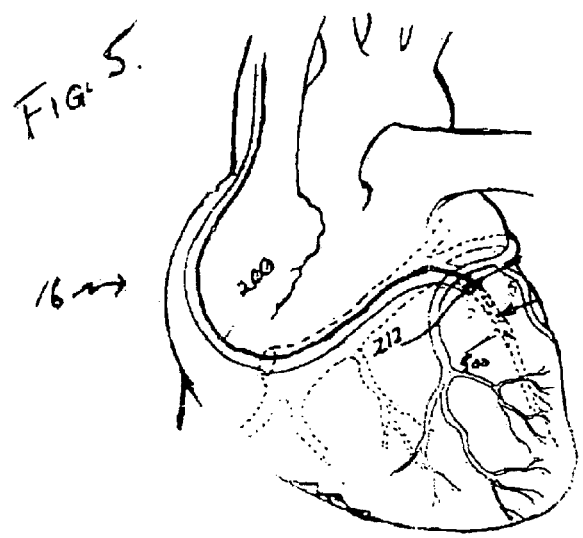
FIG. 5 schematically illustrates the lead of FIGS. 2 and 4 positioned within a cardiac venous system.

Additionally, the vasodilation solution may be used to assist in fixing the electrode within the coronary sinus. For example, as shown in FIG. 5, the intended final site of the electrode 212 may be in a branch 500 of the coronary sinus that is relatively small in cross section. Thus, introducing the vasodilation solution through the side lumen 202 may cause the reduced-size branch to dilate sufficiently to allow the lead 200 and the electrode 212 to be inserted therein. Thereafter, when the effects of the vasodilation solution have dissipated, the branch 500 will return to its undilated dimensions, securing the electrode 212 against future movement.

In an alternative embodiment, the physician may use the side lumen 202 to fix the electrode 212 at a desired location within the coronary sinus 302 or its tributary veins by delivering an adhesive, such as cyanocrylate, therethrough. In particular, according to the alternate embodiment of the present invention, an adhesive is introduced at the proximal end portion of the lead 200 and dispensed from the side lumen 202 adjacent the distal end portion of the lead 200. Once the lead 200 and the electrode 212 are positioned at an appropriate location, the physician may dispense a relatively small amount of adhesive through the side lumen 202, which upon exiting the side lumen 202 may collect on an exterior surface of the lead 200 and on an interior surface of the vein. When the adhesive cures, the lead 200 and the electrode 212 may have its position relatively fixed. Embodiments of the present invention can be used to perform a plurality of cardiac therapy functions.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method for positioning an implantable medical electrical lead body in a cardiac vein, comprising:

delivering a medium out through a distal opening of an open lumen of a lead body of the lead; the open lumen extending generally parallel to a separate lead body conductor lumen, which extends to a distal end of the lead body, and including a distal opening positioned in proximity to the distal end of the lead body, the distal opening directing the medium in a distal direction generally parallel to a distal end of the lead body; and fixing the distal end of the lead body within the vein by means of the delivered medium.

* * * * *